United States Patent
Deane (10) Patent No.: US 10,398,537 B2
(45) Date of Patent: Sep. 3, 2019

(54) ATTACHMENT STRUCTURE FOR A PERSONAL CARE APPLIANCE, A PERSONAL CARE APPLIANCE AND A METHOD

(71) Applicant: KONINKLIJKE PHILIPS N.V., Eindhoven (NL)

(72) Inventor: Steven Charles Deane, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 98 days.

(21) Appl. No.: 15/572,657

(22) PCT Filed: May 11, 2016

(86) PCT No.: PCT/IB2016/052698
§ 371 (c)(1),
(2) Date: Nov. 8, 2017

(87) PCT Pub. No.: WO2016/181323
PCT Pub. Date: Nov. 17, 2016

(65) Prior Publication Data
US 2018/0132987 A1 May 17, 2018

Related U.S. Application Data

(60) Provisional application No. 62/161,372, filed on May 14, 2015.

(51) Int. Cl.
*A61C 17/22* (2006.01)
*A61C 17/34* (2006.01)

(52) U.S. Cl.
CPC .......... *A61C 17/222* (2013.01); *A61C 17/221* (2013.01); *A61C 17/34* (2013.01); *A61C 17/225* (2013.01)

(58) Field of Classification Search
CPC ... A61C 17/221; A61C 17/222; A61C 17/225; A61C 17/34
USPC ....................... 15/22.1, 22.2, 22.4
See application file for complete search history.

(56) References Cited

U.S. PATENT DOCUMENTS

| | | | |
|---|---|---|---|
| 3,369,265 A * | 2/1968 | Halberstadt | A61C 17/32 15/145 |
| 2005/0108838 A1 | 5/2005 | Schaefer et al. | |
| 2010/0251493 A1 | 10/2010 | Sale et al. | |

(Continued)

FOREIGN PATENT DOCUMENTS

| CN | 101856275 A | 10/2010 |
|---|---|---|
| JP | H02504528 A | 12/1990 |
| JP | 2005312617 A | 11/2005 |

(Continued)

*Primary Examiner* — Randall E Chin (57) ABSTRACT

There is provided an attachment structure for a personal care appliance, the attachment structure comprising a body having a proximal end and a distal end, wherein the proximal end has a coupling receptacle that is for coupling to a drive shaft of a handle of the personal care appliance; and wherein the coupling receptacle has one or more portions of shear-thickening material on an interior surface thereof. A corresponding personal care appliance and method of securing an attachment structure to a handle of a personal care device are also provided.

15 Claims, 4 Drawing Sheets

(56) References Cited

U.S. PATENT DOCUMENTS

2013/0125320 A1* 5/2013 Bovenkamp ....... A61C 17/3481
15/22.1

FOREIGN PATENT DOCUMENTS

WO        8912182 A1    12/1989
WO    2010093632 A1    8/2010

* cited by examiner

ATTACHMENT STRUCTURE FOR A PERSONAL CARE APPLIANCE, A PERSONAL CARE APPLIANCE AND A METHOD

CROSS-REFERENCE TO PRIOR APPLICATIONS

This application is the U.S. National Phase application under 35 U.S.C. § 371 of International Application No. PCT/IB2016/052698, filed on May 11, 2016 which claims the benefit of U.S. Provisional Patent Application No. 62/161,372, filed on May 14, 2015. These applications are hereby incorporated by reference herein.

TECHNICAL FIELD

The present embodiments relate generally to personal care appliances, such as power toothbrushes, and more particularly, to an attachment structure for a personal care appliance, such as a toothbrush head.

BACKGROUND

In conjunction with oral healthcare, a primary principle of plaque removal with a toothbrush (e.g., a power toothbrush) is to get sufficient bristle tip pressure to the toothbrush head. Optimizing power transfer from the motor to the brush head is one mechanism for achieving this goal. Similar goals of maximizing power transfer efficiency are also desired with other types of personal care appliances.

Generally, a toothbrush head must be coupled to a toothbrush handle by a mechanism that both allows easy removal and replacement, while preventing the toothbrush head falling off while in use. However it must not be loose and as a result rattle and amplify vibrations that impact on the user experience. This involves compromises in design, in particular the clearance tolerances allowed between a drive shaft of the handle of the toothbrush, and the corresponding fitting of the toothbrush head. There must be sufficient clearance that the two parts are easily coupled and separated over all parts made, but if the tolerances are too large, then there will be rattling during use while the drive shaft is imparting drive forces to the brush head, enabling the cleaning action. This rattling can detract from the user experience of using the toothbrush.

Figure 1:
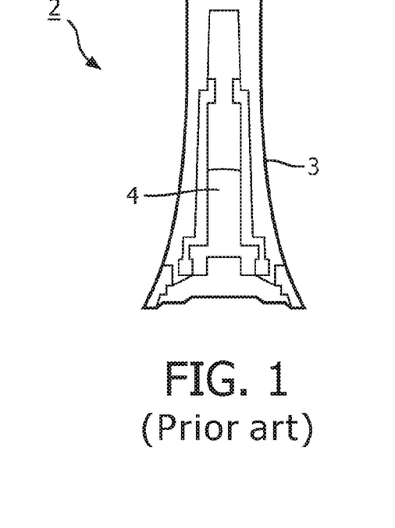
FIG. 1 is a cut-away cross-sectional view of the lower interior portion of an attachment structure of the prior art.

FIG. 1 shows a cutaway side view of the lower interior portion of a conventional toothbrush head 2. The toothbrush head 2 has a body 3 with a coupling receptacle or cavity 4 that is shaped to receive a drive shaft of the handle. The conventional toothbrush head 2 is designed to fit on to the end of the drive shaft by means of a press fit.

Thus, in view of the above problems, improvements to personal care appliances and attachment structures for personal care appliances are desired.

SUMMARY

In accordance with one aspect, an attachment for a personal care appliance is disclosed which includes the use of non-Newtonian materials in the mechanism coupling the brush head to the motor and drive train as an innovative way of getting optimal efficiency and keeping the brush head secure to the drive train. The embodiments of the present disclosure advantageously provide novel ways for implementing such mechanisms, using current manufacturing technologies, and how these benefits could be modelled and optimized.

According to one embodiment, a personal care appliance comprises a handle, a motor controller, and an attachment. The handle includes a drive train and a drive shaft. The motor controller is configured for controlling operation of the drive train to produce a mechanical stimulus. The attachment has a body with a principal axis extending between a proximal end and a distal end of the attachment, wherein the proximal end couples to the drive shaft and wherein the distal end couples to an attachment structure, such as a brush head, removably coupled thereto. When the drive train is activated, the attachment structure attached thereto is operated to provide personal care, such as tooth brushing motion. Some portion(s) of the coupling between the attachment structure and the drive train are made from a non-Newtonian material that can achieve a good coupling, with the material changing rigidity when high frequency vibrations are applied via the drive train motion to retain good coupling and provide good power transfer from the drive train to the attachment structure coupled thereto.

In accordance with a first specific aspect, there is provided an attachment structure for a personal care appliance, the attachment structure comprising a body having a proximal end and a distal end, wherein the proximal end has a coupling receptacle that is for coupling to a drive shaft of a handle of the personal care appliance; and wherein the coupling receptacle has one or more portions of shear-thickening material on an interior surface thereof.

According to a second specific aspect, there is provided a personal care appliance comprising: a handle including a drive train and a drive shaft; a motor controller for controlling operation of the drive train to produce a mechanical stimulus; and an attachment structure as described above.

According to a third specific aspect, there is provided a personal care appliance comprising a handle including a drive train and a drive shaft; a motor controller for controlling operation of the drive train to produce a mechanical stimulus; and one or more portions of shear-thickening material on the drive shaft.

According to a fourth specific aspect, there is provided a method of securing an attachment structure to a handle of a personal care appliance, the method comprising: providing one or more portions of a shear-thickening material on one of an interior surface of a coupling receptacle of the attachment structure and a drive shaft of the handle; placing the attachment structure on to the drive shaft of the handle such that the drive shaft and interior surface of the coupling receptacle contacts the shear-thickening material; and controlling, via a motor controller, operation of a drive train on the personal care appliance to produce a mechanical stimulus of the drive shaft to thereby increase the rigidity or viscosity of the shear-thickening material.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to the embodiments of the present disclosure, the attachment structures for use with a personal care appliance rely on vibration properties of the attachment when placed under a prescribed excitation from the drive train of the personal care appliance.

Figure 2:
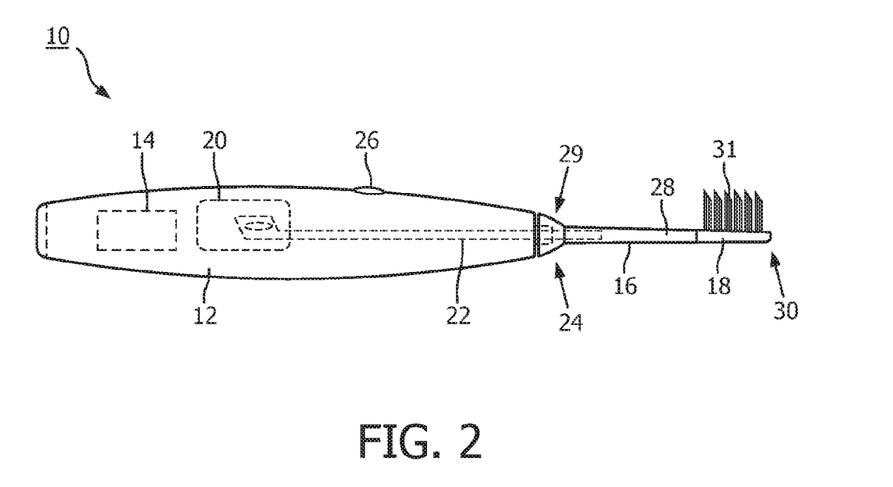
FIG. 2 is a schematic view of a personal care appliance, such as a power toothbrush, having an attachment structure according to an embodiment of the present disclosure.

With reference now to FIG. 2, there is shown a schematic view of a personal care appliance 10 of the present disclosure. According to the embodiments of the present disclosure, the personal care appliance comprises a handle 12, a motor controller 14 (that is located in the handle 12), and an attachment structure 16. In one embodiment, the attachment structure 16 comprises or is a replaceable attachment, i.e. the attachment structure 16 can be removed from the personal care appliance 10 and replaced by another attachment structure 16. The personal care appliance 10 preferably comprises or is a power toothbrush, and the attachment structure 16 preferably comprises a brush head 18. The handle 12 includes a drive train 20 and a drive shaft 22. The drive shaft 22 extends from a distal end 24 of the handle 12, and into the attachment structure 16 when an attachment structure 16 is attached to the handle 12.

Motor controller 14 (i.e., control electronics) comprises any suitable controller, microcontroller, processor, power source and/or other electronics to provide power and control signals for implementing the various functions, or any combination thereof, as discussed further herein. In addition, the personal care appliance 10 can further comprise an activation button 26 (or an equivalent mechanism) that is operable between at least (i) an OFF state and (ii) at least one activation ON state. The at least one activation ON state can comprise one or more operation states for implementing various care routines and/or operations with the personal care appliance 10.

In embodiments, motor controller 14 can be configured for controlling an operation or operations of the drive train 20 to produce a mechanical stimulus. The mechanical stimulus can comprise vibrations or other movements at a high frequency, for example, a frequency greater than 50 Hz, and for example a frequency in the range of 250-300 Hz.

Figure 3:
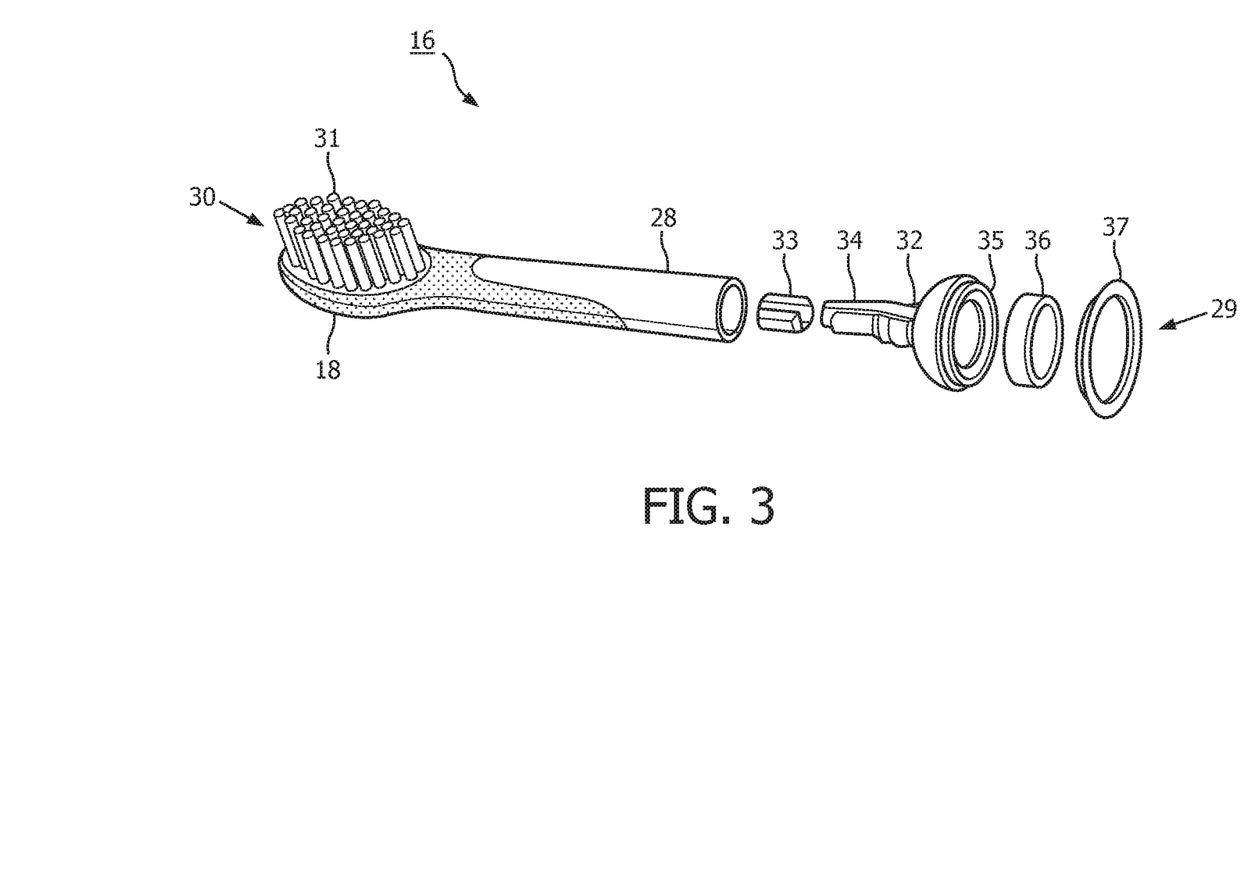
FIG. 3 shows an exploded perspective view illustration of an attachment structure.

With reference still to FIG. 2, the attachment structure 16 (which is also referred to herein as attachment) has a body 28 with a principal axis extending between a proximal end 29 and a distal end 30 of the attachment 16. The proximal end 29 couples, via a press fit or other suitable coupling mechanism (which is shown in FIG. 3), to the portion of drive shaft 22 extending from the distal end 24 of the handle 12. The distal end 30 of the attachment 16 can include brush head 18 with bristles 31, configured according to the requirements of a specific application of the attachment 16. The bristles 31 can be arranged in one or more tufts, and/or in one or more rows or columns as required for the specific application of the attachment 16. The bristles 31 can be formed from any suitable material.

In operation, responsive to the motor controller 14 operating to control an operation of the drive train 20 to produce a mechanical stimulus the attachment structure 16 implements a cleaning motion.

Turning now to FIG. 3, there is shown, an exploded perspective view illustration of an exemplary attachment structure 16 in which embodiments of the present invention can be implemented. The attachment structure 16 is designed to couple to the portion of the drive shaft 22 that extends from the distal end 24 of the handle 12 of the personal care appliance 10. The attachment structure 16 comprises a coupling mechanism located at the proximal end 29 of the attachment 16. The coupling mechanism comprises a coupling member 32 having a coupling spring 33 mounted on the distal end 34 of the coupling member 32. Coupling member 32 connects, i.e. couples, the drive shaft 22 to body 28. Mounted in a circular groove 35 in a proximal end of coupling member 32 (i.e. the end closest to proximal end 29 of the attachment structure 16) is an inertia ring 36. Mounted on the proximal end of coupling member 32 is a color ring 37 which abuts handle 12 when the attachment structure 16 is operatively positioned on the handle 12.

The inertia ring 36 is used to create a desired inertia ratio between the attachment structure 16 and the rest of the personal care appliance 10. The coupling spring 33 which mates coupling member 32 to the drive shaft 22 for transferring drive torque from drive shaft 22 to the attachment structure 16.

As noted above, the coupling mechanism should allow both easy removal and replacement, while preventing falling off while in use. The coupling mechanism must provide for efficient transfer of power from the drive mechanism to the attachment structure for optimal operation of the attachment structure. Additionally, the coupling mechanism must not be too loose, or the attachment structure will vibrate in operation, causing rattling or other noise that impacts on the user experience. Therefore, the coupling mechanism cannot be too loose nor too tight, and must also provide good power transfer from the drive mechanism to the attachment structure.

Therefore, according to embodiments of the present invention, the coupling mechanism used to couple an attachment structure 16 to a handle 12 of a personal care appliance 10 comprises one or more portions of a shear-thickening material (also known as a dilatant material, or a strain rate dependent material). A dilatant is a Non-Newtonian fluid where the shear viscosity or stiffness increases with applied shear stress. Thus, a shear-thickening material exhibits different levels of stiffness depending on the frequency of motion of the material.

Use of shear-thickening materials in the coupling mechanism for the attachment structure enables the attachment structure coupling to better conform to the size and shape of the drive shaft than existing coupling mechanisms while not in operation or while being coupled or uncoupled (such as at low strain rates, on the order of 0.1-2 Hz), and to be far stiffer at higher frequencies (e.g. greater than 50 Hz, and e.g. in the range 250-300 Hz, such as the frequencies at which a personal care appliance can operate) to transmit effectively the drive forces to the attachment structure. Thus, any rattling at the interface can be eliminated or substantially eliminated, while still allowing the attachment structure to be removed when the personal care appliance is not in use, and thus the user experience can be improved.

Dilatant materials are typically composed of stabilised suspensions of fine particles, often silica, combined with various long chain polymers to give the desired properties. They may also be incorporated into solids, by being contained in e.g. a cellular foam matrix. The behavior of the dilatant material (e.g. the magnitude of the change in stiffness, the frequency/ies of motion at which the change in stiffness occurs) can be controlled by factors such as particle size, shape and distribution. In some embodiments the dilatant material can be in the form of a foam or polymer that is soft (i.e. deformable). In specific embodiments, the dilatant material can comprise, or be, the material known as the Dow Corning® 3179 Dilatant Compound ((http://www.dowcorning.com/applications/search/products/details.aspx?prod=01512137&type=PROD). In specific embodiments, the dilatant material can comprise Dow Corning® 3179 Dilatant Compound in combination with a regular (i.e. non-dilatant) polymer. In another embodiment, the dilatant material can be the material known as D3O.

Figure 4:
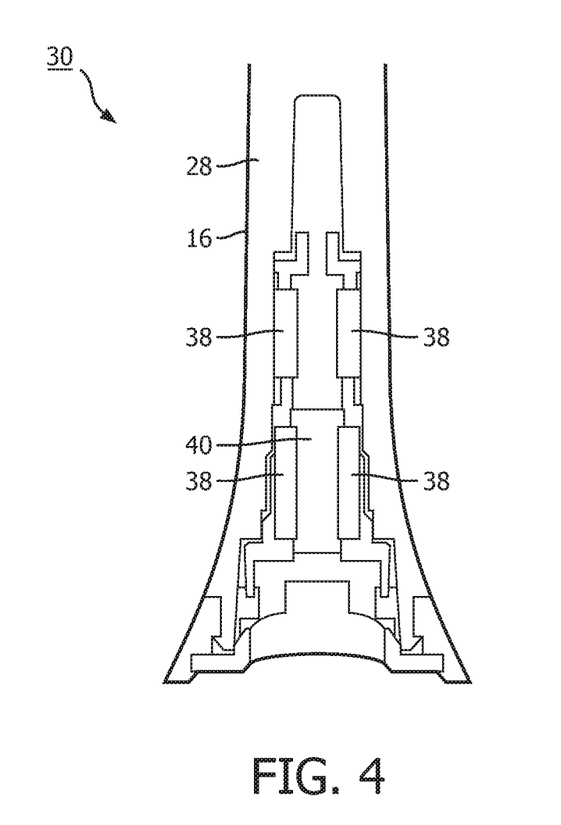
FIG. 4 is a cut-away cross-sectional view of the lower interior portion of an attachment structure of the present invention.

Referring now to FIG. 4, there is shown a cut-away side view illustration of an attachment structure 16 according to an embodiment of the present invention, in which one or more portions of non-Newtonian, or shear-thickening material 38 are used in the attachment structure 16 in the areas where the attachment structure 16 interfaces with the drive shaft 22. In particular, this shear-thickening material 38 can line the or part of the interior of the coupling receptacle 40 that is used for coupling the attachment structure 16 to the drive shaft 22. The one or more portions of shear-thickening material 38 can be on at least one surface, but preferably on several surfaces, of the coupling receptacle 40 as shown in FIG. 4. In this illustrated embodiment four portions 38 are shown, but it will be appreciated that more or less portions 38 can be used. It will also be appreciated that in some embodiments a single portion of shear-thickening material 38 can be located around the full inner circumference of the coupling receptacle 40. In some embodiments, this dilatant or shear-thickening material 38 is in the form of foam or polymer that is soft (i.e. deformable) at normal room temperature.

The coupling receptacle 40 is generally shaped to receive the drive shaft 22 and to couple the attachment structure 16 to the drive shaft 22 so that a mechanical stimulus from the drive shaft 22 is transmitted to the attachment structure 16.

In some embodiments, the size and/or position of the shear-thickening material 38 is chosen such that the space in the receptacle 40 for the drive shaft 22 to be inserted is actually slightly smaller than the minimum drive shaft 22 size. In this case, some expansion space is left inside the attachment structure coupling receptacle 40 so that the dilatant material 38 can be pushed out or deformed slightly when the drive shaft 22 is inserted into the coupling receptacle 40. This helps to provide a tight fit for the attachment structure 16, even before the appliance 10 is activated.

In some embodiments, (whether or not the space in the receptacle 40 is slightly less than the size of the drive shaft 22), a conventional attachment structure retaining system may be used to prevent 'walk off' of the attachment structure 16 during use of the appliance 10. In some embodiments, this retaining system can be a spring-clip based retaining system, for example as shown in FIG. 3. In a spring-clip based retaining system, one or more clips/coupling springs 33 can be provided in the receptacle 40 that are configured to interface with a protrusion or indentation on the drive shaft 22 when the attachment structure 16 is attached to the drive shaft 22.

Thus, when the drive mechanism 20, 22 in the handle 12 is activated, the rigidity or viscosity of the one or more portions of the shear-thickening material 38 increases as a result of the high frequency vibrations, resulting in an improved coupling of the drive forces to the attachment structure 16 compared to a conventional coupling mechanism, with little damping or loss of the vibrations. In addition, it will be appreciated that the use of the shear-thickening material 38 still allows the attachment structure 16 to be easily removed from the handle 12 when the appliance 10 is not in use.

Figure 5:
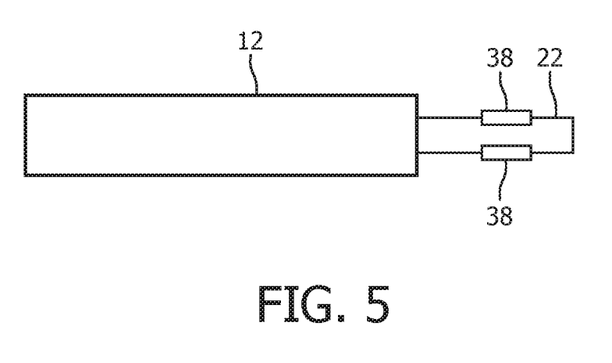
FIG. 5 is a schematic view of a personal care appliance, such as a power toothbrush, according to an embodiment of the present disclosure.

In an alternative embodiment to the above embodiments in which the dilatant material 38 is located in the coupling receptacle 40 of the attachment structure 16, it is possible for dilatant material 38 to be provided on or in the drive shaft 22 of the handle 12 instead. This embodiment is illustrated in FIG. 5, which shows a handle 12 generally as described above with reference to FIG. 2, and a drive shaft 22 that has one or more portions of shear-thickening material 38 attached thereto. In this illustrated embodiment two portions 38 are shown, but it will be appreciated that more or less portions 38 can be used. In this embodiment the handle 12 can be coupled with conventional attachment structures 2, for example as shown in FIG. 1, in order to achieve the benefits of the present invention. The portions 38 are positioned on the drive shaft 22 such that they are pressed against the interior surface of the coupling receptacle 4. When the appliance 10 is activated, the high frequency vibration generated by the drive train 20 to the drive shaft 22 results in the viscosity or rigidity of the portions 38 increasing, thereby improving the coupling of the drive shaft 22 to the attachment structure 2 and the transmission of the vibration energy to the attachment structure 2, while still enabling the attachment structure 2 to be easily removed from the handle 12 when the appliance 10 is not in use.

Figure 6:
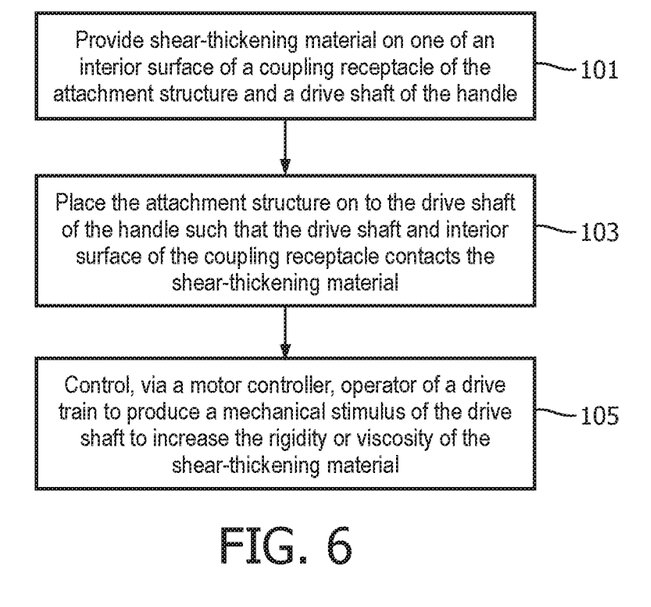
FIG. 6 is a flow chart illustrating a method of securing an attachment structure to a handle of a personal care appliance according to an embodiment.

FIG. 6 illustrates a method of securing an attachment structure to a handle of a personal care appliance according to embodiments of the invention. Firstly, a handle 12 and an attachment structure are provided. Then, in step 101, one or more portions of shear-thickening material 38 are provided. In some embodiments (for example as described above with reference to FIG. 4), the one or more portions of shear-thickening material 38 are provided on an interior surface of the attachment structure 16, e.g. an interior surface of a coupling receptacle 40 of the attachment structure 16. In other embodiments (for example as described above with reference to FIG. 5), the one or more portions of shear-thickening material 38 are provided on the drive shaft 22.

Next, in step 103, the attachment structure is placed on to the drive shaft 22 of the handle 12 such that the drive shaft 22 and the interior surface of the attachment structure contact the shear-thickening material 38. In some embodiments, this placement of the attachment structure on to the drive shaft 22 of the handle 12 can result in the engagement of a conventional retaining mechanism to hold the attachment structure on to the handle 12.

Then, in step 105, a motor controller 14 of the handle 12 is used to control operation of a drive train 20 to produce a mechanical stimulus of the drive shaft 22 to thereby increase the rigidity or viscosity of the shear-thickening material 38. This increase in the rigidity or viscosity of the shear-thickening material 38 improves the coupling of the attachment structure to the drive shaft 22, and thus improves the transmission of the vibration energy to the attachment structure, while still enabling the attachment structure to be easily removed from the handle 12 when the appliance 10 is not in use.

Attachments such as brush heads on a drive train for a Philips Sonicare® power toothbrush are the type of mechanism that would benefit from use of a shear-thickening or Non-Newtonian material 38 in at least one area of coupling between the drive mechanism coupling and the attachment structure.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in a power toothbrush for use in dental healthcare applications. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device or apparatus claim enumerating several means, several of these means may be embodied by one and the same item of hardware. The mere fact that certain measures are recited in mutually different dependent claims does not indicate that a combination of these measures cannot be used to an advantage.

Statements relating to some particular embodiments are set out below

1. A personal care appliance comprising:
   a handle including a drive train and a drive shaft;
   a motor controller for controlling operation of the drive train to produce a mechanical stimulus; and
   an attachment structure having a body with a proximal end and a distal end, wherein the proximal end has a receptacle that couples to the drive shaft, wherein shear-thickening material lines the coupling receptacle of the attachment structure on at least a portion of one interior surface thereof.

2. The personal care appliance of statement 1 wherein the shear-thickening material is the form of soft foam at room temperature without application of motion or vibration.

3. The personal care appliance of statement 1 further comprising a spring clip mechanism in the coupling mechanism.

4. The personal care appliance of statement 2 wherein the shear-thickening material becomes rigid when the vibration frequency of the drive mechanism is greater than 50 Hz.

5. An attachment structure for a personal care appliance, comprising:
   a body having a proximal end and a distal end, wherein the proximal end has a receptacle that couples to a drive shaft that forms a portion of a drive train disposed within a handle of the personal care appliance; and
   wherein the receptacle has shear-thickening material on at least a portion of one interior surface thereof.

6. The attachment structure of statement 5 wherein the shear-thickening material is the form of soft foam at room temperature without application of motion or vibration.

7. The attachment structure of statement 5 further comprising a spring clip mechanism in the coupling mechanism.

8. The attachment structure of statement 6 wherein the shear-thickening material becomes rigid when the vibration frequency of the drive mechanism is greater than 50 Hz.

9. A method of securing an attachment structure to a personal care appliance, comprising:
   controlling, via a motor controller, operation of a drive train on the personal care appliance to produce a mechanical stimulus of a drive shaft; and
   providing an attachment structure having a proximal end with a coupling for attaching to the drive shaft and wherein shear-thickening material lines the coupling on at least a portion of one interior surface thereof for ensuring a good connection between the coupling and the drive shaft.

The invention claimed is:
1. An attachment structure for a personal care appliance, the attachment structure comprising:
   a body having a proximal end and a distal end, wherein the proximal end has a coupling receptacle that is for coupling to a drive shaft of a handle of the personal care appliance; and characterised in that the coupling receptacle has one or more portions of shear-thickening material on an interior surface thereof.

2. The attachment structure of claim 1 wherein the shear-thickening material is soft or deformable without application of motion or vibration by the drive shaft.

3. The attachment structure of claim 1 wherein the shear-thickening material is in the form of a foam or polymer that is soft or deformable without application of motion or vibration by the drive shaft.

4. The attachment structure of claim 1, wherein the shear-thickening material is rigid with application of motion or vibration by the drive shaft.

5. The attachment structure of claim 1, wherein the shear-thickening material is such that the rigidity or viscosity of the shear-thickening material increases with increasing vibration frequency of the drive shaft.

6. The attachment structure of claim 5, wherein the vibration frequency is greater than 50 Hz.

7. The attachment structure of claim 5, wherein the vibration frequency is in the range of 250-300 Hz.

8. The attachment structure of any of claim 1, wherein the size and/or position of the one or more portions of shear-thickening material in the coupling receptacle is such that a space in the coupling receptacle for the drive shaft to be inserted is smaller than the size of the drive shaft.

9. The attachment structure of claim 1 further comprising a retaining mechanism in the coupling receptacle for coupling the attachment structure to the handle.

10. The attachment structure of claim 1 wherein the attachment structure is an attachment for a power toothbrush.

11. A personal care appliance comprising:
a handle including a drive train and a drive shaft;
a motor controller for controlling operation of the drive train to produce a mechanical stimulus; and
an attachment structure as claimed in claim 1.

12. A personal care appliance comprising:
a handle including a drive train and a drive shaft;
a motor controller for controlling operation of the drive train to produce a mechanical stimulus; and characterised in comprising
one or more portions of shear-thickening material on the drive shaft.

13. The personal care appliance of claim 12, further comprising:
an attachment structure comprising a body having a proximal end and a distal end, wherein the proximal end has a coupling receptacle that is for coupling to the drive shaft of the handle of the personal care appliance.

14. A method of securing an attachment structure to a handle of a personal care appliance, the method being characterised in comprising:
providing one or more portions of a shear-thickening material on one of an interior surface of a coupling receptacle of the attachment structure and a drive shaft of the handle;
placing the attachment structure on to the drive shaft of the handle such that the drive shaft and interior surface of the coupling receptacle contacts the shear-thickening material; and
controlling, via a motor controller, operation of a drive train on the personal care appliance to produce a mechanical stimulus of the drive shaft to thereby increase the rigidity or viscosity of the shear-thickening material.

15. The method of claim 14 wherein the shear-thickening material is soft or deformable without the mechanical stimulus by the drive shaft.

* * * * *